United States Patent [19]

Metzger et al.

[11] Patent Number: 4,639,526

[45] Date of Patent: Jan. 27, 1987

[54] N-SUBSTITUTED 5-AMINO-1,3,4-THIADIAZOLES

[75] Inventors: Carl Metzger; Ludwig Eue; Helmuth Hack, all of Leverkusen, Fed. Rep. of Germany

[73] Assignee: Bayer Aktiengesellschaft, Leverkusen, Fed. Rep. of Germany

[21] Appl. No.: 756,284

[22] Filed: Aug. 29, 1968

[30] Foreign Application Priority Data

Sep. 19, 1967 [DE] Fed. Rep. of Germany ........ F53531

[51] Int. Cl.[4] .................... A01N 47/36; C07D 285/12
[52] U.S. Cl. ........................................ 548/140; 71/90; 548/139; 548/141
[58] Field of Search ................ 260/306.8 D; 548/140, 548/141

[56] References Cited

PUBLICATIONS

Ermili et al., *Chem. Abstracts*, 68:2863m (1.1.68).

*Primary Examiner*—Alton D. Rollins
*Attorney, Agent, or Firm*—Felfe & Lynch

[57] ABSTRACT 2-(alkyl, alkenyl and alkylmercapto)-5-[N-(alkanoyl, chloroalkanoyl, alkoxycarbonyl, phenoxy carbonyl, N'-[alkyl and alkenyl]-aminocarbonyl and N'-alkyl-N'-[alkyl and alkenyl]-aminocarbonyl)-amino]-1,3,4-thiadiazoles, i.e. 2-(alkyl, alkenyl and alkylmercapto)-5-[N-(alkanoylamino, chloroalkanoylamino, alkoxycarbonylamino, phenoxycarbonylamino, N'-[alkyl and alkenyl]-ureido and N'-alkyl-N'-[alkyl and alkenyl]-ureido)]-1,3,4-thiadiazoles, which possess herbicidal properties, and which may be produced by conventional methods.

5 Claims, No Drawings

N-SUBSTITUTED 5-AMINO-1,3,4-THIADIAZOLES

The present invention relates to and has for its objects the provision for particular new N-substituted 5-amino-1,3,4-thiadiazoles, i.e. 2-(alkyl, alkenyl and alkylmercapto)-5-[N-(alkanoyl, chloroalkanoyl, alkoxy carbonyl, phenoxy carbonyl, N-[alkyl and alkenyl]-amino carbonyl and N'-alkyl-N'-[alkyl and alkenyl]-amino carbonyl)-amino]-1,3,4-thiadiazoles, or 2-(alkyl, alkenyl and alkylmercapto)-5-[N-(alkanoylamino, chloroalkanoylamino, alkoxy carbonylamino, phenoxy carbonylamino, N'-[alkyl and alkenyl]-ureido and N'-alkyl-N'-[alkyl and alkenyl]-ureido)]-1,3,4-thiadiazoles; or N-[2-(alkyl, alkenyl and alkylmercapto)-1,3,4-thiadiazol-5-yl]- -alkyl and -chloroalkyl amides, -alkyl and -phenyl carbamates, and -N'-[alkyl and alkenyl] and -N'-alkyl-N'-[alkyl and alkenyl] ureas, which possess valuable, especially selective, herbicidal properties, active compositions in the form of mixtures of such compounds with solid and liquid dispersible carrier vehicles, and methods for producing such compounds and for using such compounds in a new way, especially for combating weeds, undesired plants, and the like, with other and further objects becoming apparent from a study of the within specification and accompanying examples.

It is already known that thiazolyl ureas, e.g. N-(4-methyl-1,3-thiazol-2-yl)-N'-methyl urea (A), can be used as herbicides (see Belgian Pat. No. 679,138).

It has now been found, in accordance with the present invention, that the particular new N-substituted 5-amino-1,3,4-thiadiazoles having the general formula $$\underset{R-C\underset{S}{\overset{N=\!\!=\!\!N}{\diagup}}C-NH-CO-R'}{} \quad (I)$$

in which
R is selected from the group consisting of alkyl having 1–4 carbon atoms, alkenyl having 2–4 carbon atoms and alkylmercapto having 1–4 carbon atoms,
R' is selected from the group consisting of alkyl having 1–4 carbon atoms, chloroalkyl having 1–4 carbon atoms, alkoxy having 1–4 carbon atoms, phenoxy and $$-N\!\!\begin{array}{c}R''\\ \diagdown\\ R'''\end{array}$$

in which
R'' is selected from the group consisting of hydrogen and alkyl having 1–4 carbon atoms, and
R''' is selected from the group consisting of alkyl having 1–4 carbon atoms and alkenyl having 2–4 carbon atoms,
exhibit strong herbicidal, in particular selective herbicidal, properties.

Analogous 1,2,4-thiadiazol-5-yl ureas having particularly effective, especially selective, herbicidal activity, are disclosed and claimed in copending U.S. application Ser. No. 756,296, filed Aug. 29, 1968, now abandoned, whereas analogous carboxylic acid (1,2,4-thiadiazol-5-yl)-amides having particularly effective, especially selective, herbicidal activity, are disclosed and claimed in copending U.S. application Ser. No. 756,310, also filed Aug. 29, 1968, now U.S. Pat. No. 3,629,275.

The present invention also provides a process for the production of the compounds of formula (I) above in which a 5-amino-1,3,4-thiadiazole of the formula $$\underset{R-C\underset{S}{\overset{N=\!\!=\!\!N}{\diagup}}C-NH_2}{} \quad (IIa)$$

in which
R is the same as defined above,
[a] is reacted with an isocyanate of the formula $$R'-N=\!\!=\!\!C=\!\!=\!\!O \quad (IIb)$$

in which
R' is the same as defined above, or
[b] is reacted, in the presence of an acid binder, with an acid chloride of the formula $$\begin{array}{c}R''\\ \diagdown\\ R'''\end{array}\!\!N-\overset{O}{\overset{\|}{C}}-Hal \quad (IIc)$$

in which
R'' and R''' are the same as defined above, and
Hal is halogen, especially chloro, or
[c] is reacted in the presence of an acid binder, with an acid chloride of the formula $$R'-\overset{O}{\overset{\|}{C}}-Hal \quad (IId)$$

in which
R' is the same as defined above, and
Hal is halogen, especially chloro, or
[d] is reacted with an acid anhydride of the formula $$\underset{O=\!\!C-O-C=\!\!O}{\overset{R'\quad R'}{\overset{|\quad\;\;|}{}}} \quad (IIe)$$

in which
R' is the same as defined above.

The process may be carried out optionally in an inert solvent, the term solvent including mere diluents.

It is decidedly surprising that the instant new 5-amino-1,3,4-thiadiazoles exhibit a stronger herbicidal activity, and, in particular also better selective herbicidal effects, than the previously known thiadiazoles.

The instant new 5-amino-1,3,4-thiadiazoles are clearly characterized by the formula (I) above.

If 3-n-propyl-5-amino-1,3,4-thiadiazole and methyl isocyanate are used as starting materials, the reaction according to the process variant [a] can be represented by the following formula scheme:

$$\underset{\text{(IIaa)}}{n\text{-}C_3H_7-\overset{N\text{---}N}{\underset{S}{\overset{\|\quad\;\;\|}{}}}-NH_2} + \underset{\text{(IIbb)}}{O=\!\!C=\!\!N-CH_3} \longrightarrow$$

-continued

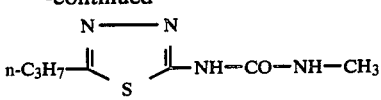

(1₁)

If dimethylcarbamic acid chloride is reacted with the same thiadiazole, the reaction according to process variant [b] can be represented by the following formula scheme:

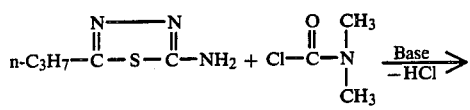

(IIaa)   (IIcc)

(2₁)

Process variant [c] proceeds in analogous manner.

The reaction according to process variant [d] corresponds to the following formula scheme:

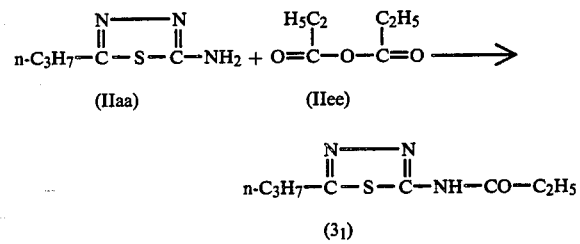

(IIaa)   (IIee)

(3₁)

Advantageously, in accordance with the present invention, in the various formulae herein:

R represents
  alkyl having 1–4 carbon atoms such as methyl, ethyl, n- and iso-propyl, n-, iso, sec-and tert-butyl, and the like, especially $C_{1-3}$ alkyl, and particularly n- and iso-propyl; or
  alkenyl having 2–4 carbon atoms such as vinyl, α-allyl (i.e., prop-2-enyl), β-allyl (i.e., 1-methyl vinyl), γ-allyl (i.e., prop-1-enyl), but-1-enyl, but-2-enyl (i.e., crotyl), but-3-enyl, methallyl (i.e., 2-methyl-prop-2-enyl), isobutenyl (i.e., 2-methyl-prop-1-enyl), and the like, especially $C_3$ alkenyl, more especially γ-, β- and γ-allyl, and particularly γ-allyl; or
  alkylmercapto having 1–4 carbon atoms, such as methyl to tert-butyl inclusive, as defined above, and the like, -mercapto;

R' represents
  alkyl having 1–4 carbon atoms, such as methyl to tert.-butyl inclusive, as defined above, and the like, especially $C_{1-2}$ alkyl, and particularly ethyl; or
  chloroalkyl having 1–4 carbon atoms, such as chloro-substituted methyl to tert.-butyl inclusive, as defined above, and the like, espeically 1-2 chloro-substituted $C_{1-4}$ alkyl, and particularly mono and di chloromethyl; or alkoxy having 1–4 carbon atoms, such as methoxy, ethoxy, n- and iso-propoxy, n-, iso-, sec.- and tert.-butoxy and the like, especially $C_{1-3}$ alkoxy; or phenoxy; or

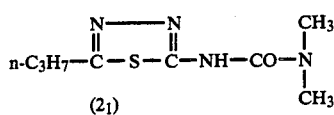

in which
R" represents
  hydrogen; or
  alkyl having 1–4 carbon atoms, such as methyl to tert.-butyl inclusive, as defined above, and the like, especially $C_{1-3}$ alkyl, and particularly methyl; and
R''' represents
  alkyl having 1–4 carbon atoms, such as methyl to tert.-butyl inclusive, as defined above, and the like, especially $C_{1-3}$ alkyl; or
  alkenyl having 2–4 carbon atoms, such as vinyl to isobutenyl, as defined above, and the like, especially $C_3$ alkenyl, more especially α-, β- and γ-allyl, and particularly α-allyl.

In accordance with a particular feature of the present invention, R represents $C_{1-4}$, especially $C_{1-3}$, alkyl, or $C_3$ alkenyl, or $C_{1-4}$ alkylmercapto; R' represents $C_{1-4}$, especially $C_{1-2}$, alkyl, or 1–2 chloro-substituted $C_{1-4}$ alkyl, especially mono and di chloromethyl, or $C_{1-4}$, especially $C_{1-3}$, alkoxy, or phenoxy, or

in which R" represents hydrogen, or $C_{1-3}$ alkyl, especially methyl; and R''' represents $C_{1-3}$ alkyl, or $C_3$ alkenyl.

Some of the starting aminothiadiazoles of formula (IIa) are already known. New thiadiazoles of this type can be prepared in the same manner as those already known, for example by reaction of the appropriate 1-acylthiosemicarbazides with agents which split off water, such as acetic anhydride [see Chemischer Bericht 29, 2511 (1896)].

The starting materials corresponding to formulae (IIb), (IIc), (IId) and (IIe) are also known.

Examples of the preferred isocyanates which can be used are methyl isocyanate, ethyl isocyanate, isopropyl iso-cyanate, and the like.

Examples of the preferred acid chlorides which can be used are dimethylcarbamyl chloride, propionyl chloride, monochloroacetyl chloride, dichloroacetyl chloride, methyl chloroformate, and the like.

As solvents, all inert organic solvents are suitable. Preferred solvents include hydrocarbons, such as benzene, toluene; ethers, such as diethyl ether, dioxan, tetrahydrofuran; chlorinated hydrocarbons, such as methylene chloride, chloroform, carbon tetrachloride; ketones, such as acetone; esters, such as ethyl acetate and acetonitrile; and dimethyl formamide; and the like.

As acid binders, all customary acid-binding agents can be used. Preferred agents include the alkali metal hydroxides, alkali metal carbonates and tertiary amines. Particularly suitable are sodium hydroxide, sodium carbonate, triethyl amine and pyridine.

The reaction temperatures can be varied within a fairly wide range. In general, the work is carried out at substantially between about 0°–140° C., preferably between about 10°–120° C.

When carrying out the production process, approximately equimolar amounts of starting materials are generally used. The working up of the reaction mixture is carried out in the usual manner.

Advantageously, the active compounds according to the present invention influence plant growth and can therefore be used for defoliation or for desiccation of the green parts of plants. In this case they serve as harvest auxiliaries to facilitate harvesting. They are, however, quite particularly suitable for the control of weeds. By weeds are meant in the widest sense all plants which grow in places where they are not desired. Whether the active compounds according to the present invention act as total or selective herbicides depends essentially on the amount applied, as the artisan will appreciate.

The active compound according to the present invention can be used for example in the case of the following plants: dicotyledons, such as mustard (Sinapis), cress (Lepidium), cleaver (Galium), common chickweed (Stellaria), mayweed (Matricaria), smallflower Galinsoga (Galinsoga), fathen (Chenopodium), stinging nettles (Urtica), groundsel (Senecio), cotton (Gossypium), beets (Beta), beans (Phaseolus), carrots (Daucus), potatoes (Solanum), coffee (Coffea); monocotyledons, such as timothy (Phleum), bluegrass (Poa), fescue (Festuca), goosegrass (Eleusine), foxtail (Setaria), ryegrass (Lolium), cheat (Bromus), barnyard grass (Echinochloa), maize (Zea), rice (Oryza), oats (Avena), barley (Hordenum), wheat (Triticum), millet (Panicum), and sugar cane (Saccharum); and the like.

The active compounds according to the instant invention can be utilized, if desired, in the form of the usual formulations or compositions with conventional pesticide diluents or extenders, i.e., dispersible carrier vehicles, such as solutions, emulsions, suspensions, emulsifiable concentrates, spray powders, pastes, soluble powders, dusting agents, granules, etc. These are prepared in known manner, for instance by extending the active compounds with dispersible liquid diluent carriers and/or dispersible solid carriers optionally with the use of carrier vehicle assistants, e.g., surface-active agents, including, emulsifying agents and/or dispersing agents, whereby, for example, in the case where water is used as diluent, organic solvents may be added as auxiliary solvents. The following may be chiefly considered for use as carrier vehicles for this purpose: dispersible liquid diluent carriers including inert organic solvents such as aromatic hydrocarbons (e.g. benzene, toluene, xylene, etc.), halogenated, especially chlorinated, aromatic hydrocarbons (e.g. chlorobenzenes), paraffins (e.g. petroleum fractions), chlorinated aliphatic hydrocarbons (e.g. methylene chloride, etc.), alcohols (e.g. methanol, ethanol, propanol, butanol, etc.), ethers, ether-alcohols (e.g. glycol monomethyl ether, etc.), amines (e.g. ethanolamine, etc.), amides (e.g. dimethyl formamide, etc.), sulfoxides (e.g. dimethyl sulfoxide, etc.) ketones (e.g. acetone, etc.), and/or water; as well as dispersible finely divided solid carriers, such as ground natural minerals (e.g. kaolins, alumina, silica, chalk, i.e., calcium carbonate, talc, kieselguhr, etc.), and ground synthetic minerals (e.g. highly dispersed silicic acid, silicates, e.g., alkali silicates, etc.); whereas the following may be chiefly considered for use as carrier vehicle assistants, e.g., surface-active agents, for this purpose: emulsifying agents, such as nonionic and/or anionic emulsifying agents (e.g. polyethylene oxide esters of fatty acids, polyethylene oxide ethers of fatty alcohols, alkyl sulfonates, aryl sulfonates, etc., and especially alkyl arylpolyglycol ethers, magnesium stearate, sodium oleate, etc.); and/or dispersing agents, such as lignin, sulfite waste liquors, methyl cellulose, etc.

As will be appreciated by the artisan, the active compounds according to the instant invention may be employed alone or in the form of mixtures with one another and/or with such solid and/or liquid dispersible carrier vehicles and/or with other known compatible active agents, especially plant protection agents, such as other herbicides, fungicides, insecticides, bactericides, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.01–5%, preferably 0.25–1%, by weight of the mixture. Thus, the present invention contemplates over-all compositions which comprise mixtures of a dispersible carrier vehicle such as (1) a dispersible carrier solid, and/or (2) a dispersible carrier liquid such as an inert organic solvent and/or water preferably including a surface active effective amount of a conventional pesticide carrier vehicle assistant, e.g., a surface-active agent, such as an emulsifying agent and/or a dispersing agent, and an amount of the active compound which is effective for the purpose in question and which is generally between about 0.01–95% by weight of the mixture.

While the active compounds can be used according to the pre-emergence method, they are also effective when used according to the post-emergence method, i.e. both before and after the emergence of the plants.

In general, the amounts of the active compound actually applied, preferably according to the pre-emergence method, are substantially between about 1–50 kg/hectare, apart from any carrier vehicle which may also be present, whereas concentrations of substantially between about 0.01–5%, preferably 0.25–1%, by weight of the active compound in carrier vehicle compositions are applied in particular where formulations are used, preferably according to the post-emergence method.

The active compounds can also be used in accordance with the well known ultra-low-volume process with good success, i.e. by applying such compound if normally a liquid, or by applying a liquid composition containing the same, via very effective atomizing equipment in extremely finely divided form, i.e. mist form, for example by airplane crop spraying techniques. Only a few liters/hectare are needed, and often amounts up to about 1 quart/acre, preferably 2–16 fluid ounces/acre, are sufficient. In this process it is possible to use highly concentrated liquid compositions with said liquid carrier vehicles containing from about 40 to about 95% by weight of active compound or even the 100% active substance alone, e.g. about 40–100% by weight of the active compound.

Furthermore, the present invention contemplates methods of selectively controlling or combatting undesired plants, e.g., weeds and the like, and/or of defoliating plants, which comprise applying to at least one of (a) such weeds, plants, etc. and (b) their habitat, i.e., the locus to be protected, a herbicidally effective, or defoliating, amount of the particular active compound of the invention alone or together with a carrier vehicle as noted above. The instant formulations or compositions are applied in the usual manner, for example, by spraying, atomizing, scattering, dusting, watering, sprinkling, and the like, whether for pre-emergence application to the soil or post-emergence application to the weeds.

It will be realized, of course, that in connection with the pre-emergence use of the instant compounds as well as the post-emergence use thereof, the concentration of the particular active compound utilized in admixture with the carrier vehicle will depend upon the intended application and may be varied within a fairly wide range depending upon the weather conditions, the purpose for which the active compound is used, e.g. selective or total herbicide, and the plants which are to be controlled or protected. Therefore, in special cases, it is possible to go above or below the aforementioned concentration ranges and amounts/hectare.

The following Examples illustrate, without limitation, the herbicidal activity of the particular active compounds of the present invention.

EXAMPLE 1

Pre-emergence test

Solvent: 5 parts by weight acetone
Emulsfier: 1 part by weight alkylaryl polyglycol ether To produce a suitable preparation of the particular active compound, 1 part by weight of such active compound is mixed with the stated amount of solvent, the stated amount of emulsifier is then added and the resulting concentrate is diluted with water to the desired final concentration.

Seeds of the test plants are sown in normal soil and, after 24 hours, watered with the given active compound preparation. It is expedient to keep constant the amount of water per unit area. The concentration of the active compound in the preparation is of no importance, only the amount of active compound applied per unit area being decisive. After three weeks, the degree of damage to the test plants is determined and characterized by the values of 0–5 which have the following meaning:

```
0 no effect
1 slight damage or delay in growth
2 marked damage or inhibition of growth
3 heavy damage and only deficient development
  or only 50% emerged
4 plants partially destroyed after germination
  or only 25% emerged
5 plants completely dead or not emerged.
```

The particular active compounds tested, the amounts applied and the results obtained can be seen from the following Table 1:

TABLE 1

| Active Compound | Pre-emergence Test Amount of Active Compound applied in kg/hectare | Echino-chloa | Cheno-podium | Sinapis | Cotton | Wheat |
|---|---|---|---|---|---|---|
| (A) $CH_3-C\!=\!\!=\!\!N$ ; $HC-S-C-NH-CO-NHCH_3$ (known) | 40 | 4–5 | 5 | 5 | 4 | 4–5 |
| | 20 | 4 | 5 | 5 | 4 | 4 |
| | 10 | 4 | 5 | 4 | 3 | 4 |
| | 5 | 3 | 4 | 2–3 | 1 | 3 |
| | 2.5 | 2 | 2–3 | 1 | 0 | 1 |
| (4$_1$) $CH_3$ $N\!=\!\!=\!\!N$ ; $CH_3-CH-C-S-C-NH-CO-NH-CH_3$ | 40 | 5 | 5 | 5 | 5 | 5 |
| | 20 | 5 | 5 | 5 | 3 | 5 |
| | 10 | 5 | 5 | 5 | 3 | 5 |
| | 5 | 5 | 5 | 5 | 1 | 4 |
| | 2.5 | 4 | 4–5 | 5 | 0 | 3 |
| (5$_1$) $N\!=\!\!=\!\!N$ ; $CH_3-S-C-S-C-NH-CO-NH-CH_3$ | 40 | 5 | 5 | 5 | 5 | 4–5 |
| | 20 | 5 | 5 | 5 | 5 | 4–5 |
| | 10 | 5 | 5 | 5 | 5 | 4–5 |
| | 5 | 5 | 5 | 5 | 3 | 3 |
| | 2.5 | 5 | 5 | 5 | 3 | 0 |

EXAMPLE 2

Post-emergence test

Solvent: 5 parts by weight acetone
Emulsifier: 1 part by weight alkylaryl polyglycol ether To produce a suitable preparation of the particular active compound, 1 part by weight of such active compound is mixed with the stated amount of solvent, the stated amount of emulsifier is then added and the resulting concentrate is diluted with water to the desired final concentration.

Test plants which have a height of about 5–14 cm. are sprayed with the given active compound preparation until just dew moist. After three weeks, the degree of damage to the plants is determined and characterized by the values 0–5, which have the following meaning:

```
0 no effect
1 a few slightly burnt spots
2 marked damage to leaves
3 some leaves and parts of stalks
  partially dead
4 plant partially destroyed
5 plant completely dead
```

The particular active compounds tested, their concentrations and the results obtained can be seen from the following Table 2:

TABLE 2

| Active Compound | Concentration of Active Compound in % | Post-emergence Test Echinochloa | Chenopodium | Sinapis | Stellaria | Galinsoga | Daucus | Oats | Cotton | Wheat |
|---|---|---|---|---|---|---|---|---|---|---|
| (A) CH₃—C═══N ‖ ‖ HC—S—C—NH—CO—NH—CH₃ (known) | 0.2 | 5 | 5 | 5 | 5 | 5 | 5 | 2 | 3 | 2 |
| | 0.1 | 4 | 5 | 5 | 4–5 | 5 | 3 | 1–2 | 2–3 | 1–2 |
| | 0.05 | 3 | 4–5 | 4–5 | 3 | 4–5 | 1 | 1 | 2 | 1 |
| | 0.025 | 1 | 3 | 4 | 2 | 3 | 0 | 0 | 0 | 0 |
| (1₂) n-C₃H₇—C—S—C—NH—CO—NH—CH₃ | 0.2 | 5 | 5 | 5 | 5 | 5 | 5 | 5 | 4 | 3 |
| | 0.1 | 5 | 5 | 5 | 5 | 5 | 5 | 5 | 4 | 3 |
| | 0.05 | 3 | 4–5 | 5 | 5 | 4–5 | 4 | 4–5 | 3 | 3 |
| | 0.025 | 1 | 3 | 5 | 4 | 3 | 3 | 3 | 2 | 2 |
| (4₂) CH₃—CH—C—S—C—NH—CO—NH—CH₃ | 0.2 | 4–5 | 5 | 5 | 5 | 5 | 5 | 5 | 4–5 | 5 |
| | 0.1 | 4–5 | 5 | 5 | 5 | 5 | 5 | 4 | 4 | 3 |
| | 0.05 | 4–5 | 5 | 5 | 5 | 5 | 5 | 3 | 2 | 2 |
| | 0.025 | 4–5 | 5 | 5 | 4–5 | 5 | 4 | 0 | 1 | 0 |
| (5₂) CH₃—S—C—S—C—NH—CO—NH—CH₃ | 0.2 | 5 | 5 | 5 | 5 | 5 | 5 | 4–5 | 5 | 2 |
| | 0.1 | 5 | 5 | 5 | 5 | 5 | 5 | 4 | 5 | 1 |
| | 0.05 | 5 | 5 | 5 | 5 | 5 | 5 | 4 | 4–5 | 0 |
| | 0.025 | 4–5 | 5 | 5 | 5 | 5 | 5 | 4 | 4–5 | 0 |
| (6₁) n-C₄H₉S—C—S—C—NH—CO—NH—CH₃ | 0.2 | 5 | 5 | 5 | 5 | 5 | 4 | 5 | 2 | |
| | 0.1 | 5 | 5 | 5 | 5 | 5 | 4 | 4–5 | 1–2 | |
| | 0.05 | 5 | 5 | 5 | 5 | 5 | 5 | 3 | 4 | 0 |
| | 0.025 | 4–5 | 5 | 5 | 5 | 5 | 5 | 3 | 3 | 0 |
| (7₁) CH₃S—C—S—C—NH—CO—C₂H₅ | 0.2 | 5 | 5 | 5 | 5 | 5 | 5 | 4–5 | 5 | 3 |
| | 0.1 | 5 | 5 | 5 | 5 | 5 | 5 | 3 | 5 | 1 |
| | 0.05 | 4 | 5 | 5 | 5 | 5 | 5 | 3 | 4 | 0 |
| | 0.025 | 3 | 4 | 5 | 3 | 5 | 5 | 1 | 3 | 0 |

EXAMPLE 3

(Reaction [a])

To 14.9 g (0.1 mol) 2-n-propyl-5-amino-1,3,4-thiadiazole dissolved in 100 ml dimethyl formamide there are added dropwise, at 20° C., 5.7 g (0.1 mol) methyl isocyanate. After the subsidence of the heat effect, stirring is continued for 1 hour at 50° C., and distillation to one half of the original volume is then effected in a vacuum, followed by pouring into 400 ml of water. The crude N-(2-n-propyl-1,3,4-thiadiazol-5-yl)-N'-methyl urea (1₃) is obtained in solid form and is filtered off with suction.

In analogous manner, the further ureas mentioned in Table 3, based on Formula (I) above, were also prepared.

TABLE 3

| | R | R" | R''' | M.p. °C. |
|---|---|---|---|---|
| (8₁) | CH₃ | H | CH₃ | 259 |
| (9₁) | CH₃ | H | C₂H₅ | 156 |
| (10₁) | C₂H₅ | H | CH₃ | 178 |
| (11₁) | n-C₃H₇ | H | C₂H₅ | 98 |
| (4₃) | iso-C₃H₇ | H | CH₃ | 147 |
| (12₁) | iso-C₃H₇ | H | C₂H₅ | 172 |
| (13₁) | CH₃—CH═CH— | H | CH₃ | 196 |
| (5₃) | CH₃S | H | CH₃ | 212 |
| (14₁) | CH₃S | H | C₂H₅ | 136 |
| (15₁) | CH₃S | H | n-C₃H₇ | 125 |
| (16₁) | CH₃S | H | CH₂═CH—CH₂— | 196 |
| (6₂) | n-C₄H₉S | H | CH₃ | 154 |

EXAMPLE 4

(Reaction [c])

To 28.6 g (0.2 mol) 2-isopropyl-5-amino-1,3,4-thiadiazole in 200 ml dioxan there are added 20.2 g (0.2 mol) ethyl amine, and 22.6 g (0.2 mol) chloroacetyl chloride are slowly added dropwise at 20° C. Stirring is then effected for 2 hours at 50° C., followed by suction filtration from the precipitate, and the filtrate is stirred into 400 ml of water. The N-(2-isopropyl-1,3,4-thiadiazol-5-yl)-chloroacetamide (17₁) separates in solid form (See Table 4).

In analogous manner, the further amides mentioned in Table 4, based on Formula (I) above, were also prepared.

TABLE 4

| | R | R' | m.p. °C. |
|---|---|---|---|
| (17₁) | iso-C₃H₇ | CH₂Cl | 196 |
| (18₁) | CH₃ | CH₂Cl | 185 |
| (19₁) | CH₃ | CHCl₂ | 241 |
| (20₁) | C₂H₅ | CHCl₂ | 183 |
| (21₁) | n-C₃H₇ | CH₂Cl | 225 |
| (22₁) | CH₃S | CH₂Cl | 221 |

TABLE 4-continued

|  | R | R' | m.p. °C. |
|---|---|---|---|
| (23$_1$) | n-C$_4$H$_9$ | CH$_2$Cl | 163 |

EXAMPLE 5

(Reactions [c] and [b])

To 28.6 g (0.2 mol) 2-n-propyl-5-amino-1,3,4-thiadiazole in 200 ml dioxan there are added 20.2 g (0.2 mol) triethyl amine, and 18.9 g (0.2 mol) methyl chloroformate are added dropwise at 40° C. Stirring is then effected for 2 hours at 60° C. Thereafter, suction filtration from the triethylamine hydrochloride is effected and the filtrate is evaporated. N-(2-n-propyl-1,3,4-thiadiazol-5-yl)-methylcarbamate (24$_1$) is obtained in solid form (see Table 5).

In analogous manner, the further carbamates and ureas mentioned in Table 5, based on Formula (I) above, were also prepared.

TABLE 5

|  | R | R' | R'' | R''' | m.p. °C. |
|---|---|---|---|---|---|
| (25$_1$) | CH$_3$ | CH$_3$O |  |  | 234 |
| (26$_1$) | C$_2$H$_5$ | CH$_3$O |  |  | 177 |
| (24$_1$) | n-C$_3$H$_7$ | CH$_3$O |  |  | 138 |
| (27$_1$) | n-C$_3$H$_7$ | C$_6$H$_5$O |  |  | 187 |
| (28$_1$) | iso-C$_3$H$_7$ | CH$_3$O |  |  | 114 |
| (29$_1$) | iso-C$_3$H$_7$ | C$_6$H$_5$O |  |  | 196 |
| (2$_2$) | n-C$_3$H$_7$ |  | CH$_3$ | CH$_3$ | 71 |
| (30$_1$) | iso-C$_3$H$_7$ |  | CH$_3$ | CH$_3$ | 65 |
| (31$_1$) | n-C$_3$H$_7$ | iso-C$_3$H$_7$O |  |  | 78 |

EXAMPLE 6

(Reaction [d])

To 28.6 (0.2 mol) 2-n-propyl-5-amino-1,3,4-thiadiazole are added 26 g (0.2 mol) propionic anhydride, and heated at 120° C. for 3 hours. After evaporation of the propionic acid, the N-(2-n-propyl-1,3,4-thiadiazol-5-yl)-propionamide (3$_2$) remains in the solid form (See Table 6 below).

In analogous manner, the further amides mentioned in Table 6, based on Formula (I) above, were also prepared.

TABLE 6

|  | R | R' | m.p. °C. |
|---|---|---|---|
| (3$_2$) | n-C$_3$H$_7$ | C$_2$H$_5$ | 192 |
| (32$_1$) | CH$_3$ | C$_2$H$_5$ | 265 |
| (33$_1$) | C$_2$H$_5$ | C$_2$H$_5$ | 225 |
| (34$_1$) | iso-C$_3$H$_7$ | C$_2$H$_5$ | 194 |
| (7$_2$) | CH$_3$S | C$_2$H$_5$ | 174 |
| (35$_1$) | n-C$_4$H$_9$S | C$_2$H$_5$ | 145 |

It will be realized by the artisan that all of the foregoing compounds contemplated by the present invention possess the desired selective or total herbicidal properties, and especially the capability of selectively destroying weeds or defoliating plants, as well as a comparatively low toxicity toward warm-blooded creatures and a concomitantly low phytotoxicity at appropriate dosages with respect to higher plants, enabling such compounds to be used with correspondingly favorable compatibility with warm-blooded creatures and higher plants for more effective control and/or elimination of weeds by selective application of such compounds to such weeds and/or their habitat. Nevertheless, the instant compounds possess total herbicidal action when used in large quantities, although selective herbicidal action is obtained when used in smaller quantities. As contemplated herein, the term "weeds" is meant to include not only weeds in the narrow sense, but also in the broad sense, whereby to cover all plants and vegetation considered undesirable for the particular purposes in question.

It will be appreciated that the instant specification and examples are set forth by way of illustration and not limitation, and that various modifications and changes may be made without departing from the spirit and scope of the present invention which is to be limited only by the scope of the appended claims.

What is claimed is:

1. N-substituted 5-amino-1,3,4-thiadiazole having the formula $$R-C\underset{S}{\overset{N\text{———}N}{\underset{\|}{\|}}}C-NH-CO-N\underset{R'''}{\overset{R''}{\diagup}}$$

in which R is alkyl-mercapto having 1–4 carbon atoms, R'' is selected from the group consisting of hydrogen and alkyl having 1–4 carbon atoms, and R''' is selected from the group consisting of alkyl having 1–4 carbon atoms and alkenyl having 2–4 carbon atoms.

2. Thiadiazole according to claim 1 wherein R is alkylmercapto having 1–4 carbon atoms, R'' is selected from the group consisting of hydrogen and alkyl having 1–3 carbon atoms, and R''' is selected from the group consisting of alkyl having 1–3 carbon atoms.

3. Thiadiazole according to claim 1 wherein R is alkylmercapto having 1–4 carbon atoms, R'' is hydrogen and R''' is alkyl having from 1 to 3 carbon atoms.

4. Thiadiazole according to claim 1 wherein such compound is N-(2-methylmercapto-1,3,4-thiadiazol-5-yl)-N'-methyl urea having the formula $$CH_3-S-C\underset{S}{\overset{N\text{———}N}{\underset{\|}{\|}}}C-NH-CO-NH-CH_3$$

5. Thiadiazole according to claim 1 wherein such compound is N-(2-n-butylmercapto-1,3,4-thiadiazol-5-yl)-N'-methyl urea having the formula $$n\text{-}C_4H_9S-C\underset{S}{\overset{N\text{———}N}{\underset{\|}{\|}}}C-NH-CO-NH-CH_3$$

* * * * *